United States Patent [19]

Haller et al.

[11] Patent Number: 5,327,079

[45] Date of Patent: Jul. 5, 1994

[54] METHOD AND DEVICE FOR NON-DESTRUCTIVE TESTING OF A PENETRATION OF A REACTOR PRESSURE VESSEL LID

[75] Inventors: Hans Haller; Filippo D'Annucci, both of Mannheim, Fed. Rep. of Germany

[73] Assignee: ABB Reaktor GmbH, Mannheim, Fed. Rep. of Germany

[21] Appl. No.: 954,383

[22] Filed: Sep. 30, 1992

[30] Foreign Application Priority Data

May 13, 1992 [DE] Fed. Rep. of Germany ....... 4215700

[51] Int. Cl.⁵ ............... G01N 27/82; G01N 27/72; G01R 33/00; G21C 17/00
[52] U.S. Cl. .................... 324/219; 324/238; 324/262; 376/249
[58] Field of Search ............. 324/219, 220, 221, 237, 324/238, 240, 241, 242, 262; 376/249

[56] References Cited

U.S. PATENT DOCUMENTS

| | | |
|---|---|---|
| 4,018,082 | 4/1977 | Manoliu et al. . |
| 4,167,121 | 9/1979 | Mauch . |
| 4,757,258 | 7/1988 | Kelly, Jr. et al. . |
| 4,767,986 | 8/1988 | Törnblom , .......................... 324/237 |
| 5,036,707 | 8/1991 | Paciej . |

FOREIGN PATENT DOCUMENTS

| | | |
|---|---|---|
| 3316461 | 11/1983 | Fed. Rep. of Germany . |
| 3324444 | 1/1984 | Fed. Rep. of Germany . |
| 3411854 | 10/1984 | Fed. Rep. of Germany . |
| 2296848 | 7/1976 | France . |

Primary Examiner—Walter E. Snow

[57] ABSTRACT

Previously, only webs between connectors in reactor pressure vessel lids have been examined for incipient cracks by using an ultrasonic scanning head. In order to be able to test the connector penetrated by a bush from an annular gap formed between the connector and the bush, a frame is provided which carries a housing through lockable floating bearings for receiving a rotary plate in the housing. The rotary plate is concentrically associated with a centering piece which is adjustable in the vertical direction and is eccentrically associated with a lifting cylinder which is likewise vertically adjustable. A free end of the lifting cylinder carries a probe drive for inserting a probe into the annular gap. The annular gap is scanned by the probe due to an oscillating movement of the rotary plate.

13 Claims, 10 Drawing Sheets

METHOD AND DEVICE FOR NON-DESTRUCTIVE TESTING OF A PENETRATION OF A REACTOR PRESSURE VESSEL LID

The invention relates to a method and a device for non-destructively testing a penetration in the form of a welded-in connector of a reactor pressure vessel lid placed on a depositing ring, wherein the connector is penetrated by a bush supported on the connector, defining an annular gap therebetween, and a lower end of the bush extends further into the interior of the reactor pressure vessel lid than the connector.

According to German Patent DE 26 36 246 C2, in a reactor pressure vessel lid placed on a depositing ring, webs between the connectors are examined for incipient cracks by using an ultrasonic scanning head. In that publication, no provision is made for testing the connectors themselves which are penetrated by a bush, leaving an annular gap.

It is accordingly an object of the invention to provide a method and a device for non-destructively testing a penetration in a reactor pressure vessel lid, which overcome the hereinafore-mentioned disadvantages of the heretofore-known methods and devices of this general type and which can be carried out or used with installed bushes.

With the foregoing and other objects in view there is provided, in accordance with the invention, a method of non-destructively testing a penetration in the form of a connector welded in a reactor pressure vessel lid disposed on a depositing ring, including a bush penetrating and being supported on the connector, defining an annular gap between the bush and the connector, and the bush having a lower end extending further into the interior of the reactor pressure vessel lid than the connector, which comprises introducing a probe with an eddy current scanning head into the annular gap and displacing the probe in the annular gap.

A complicated construction of the bushes is avoided by this measure.

In accordance with another mode of the invention, there is provided a method which comprises bringing a centering piece into contact with the lower end of the bush, and setting the probe in rotary movement together with the centering piece and the bush.

In this case, the centering piece serves as a carrier for the bush, so that the bush cannot hinder the rotary movement of the probe in any phase.

In accordance with a further mode of the invention, there is provided a method which comprises oscillating the probe in the rotary movement, and vertically moving the probe into a new testing position at the beginning or end of the oscillating movement.

In this case, the annular gap is scanned in continuous annular stages.

In accordance with an added mode of the invention, there is provided a method which comprises continuously vertically moving the probe during the rotary movement. If there is a constant adjusting movement of the probe during the rotary movement, the annular gap is scanned in a meandering manner.

In accordance with an additional mode of the invention, there is provided a method which comprises bringing a centering piece into contact with the lower end of the bush, scanning the annular gap with the eddy current scanning head in a band-type manner in a vertical direction while the bush remains in a position of rest, and moving the eddy current scanning head into a new testing position after scanning one band, by rotating the probe for scanning a further band. This is done if it is established during a trial rotation of the rotary plate, when the centering piece has already been placed on but the probe has not yet been inserted into the annular gap that, for incomprehensible reasons, the centering piece is spinning and the bush is not being carried along.

The present contact with the centering piece ensures that the band-type scanning provides uninterrupted test results.

With the objects of the invention in view, there is also provided, in a reactor pressure vessel having a depositing ring, a lid being disposed on the depositing ring and having an interior, a penetration in the form of a connector welded in the lid, a bush penetrating and being supported on the connector, defining an annular gap between the connector and the bush, and the bush having a lower end extending further into the interior of the lid than the connector, a device for non-destructively testing the penetration, comprising a manipulator disposed inside the depositing ring, a frame supported on the manipulator, lockable floating bearings on the frame, a housing carried by the bearings, a rotary plate received by the housing, a lifting cylinder having a free end and being eccentrically associated with the rotary plate, the lifting cylinder being vertically adjustable and carrying out a rotary movement of the rotary plate, a probe, and a probe drive disposed at the free end of the lifting cylinder for moving the probe in an axially parallel direction relative to the connector.

In accordance with another feature of the invention, there is provided a centering piece being concentrically associated with the rotary plate, the centering piece being adjustable in the vertical direction and carrying out the rotary movement of the rotary plate.

While all of the parts of the device borne by the frame are moved into a first position by the manipulator, the centering piece comes into contact with the bush with a fine vertical adjustment maintaining a predetermined pressing force. While maintaining the given pressing force, rotation of the rotary plate by up to 370° is then carried out. In this case, if the bush is carried along by the centering piece, the method is initiated by bringing the centering piece into contact with the lower end of the bush, and setting the probe in rotary movement together with the centering piece and the bush. If it is not carried along, the test is initiated by bringing the centering piece into contact with the lower end of the bush, scanning the annular gap with the eddy current scanning head in a band-type manner in a vertical direction while the bush remains in a position of rest, and moving the eddy current scanning head into a new testing position after scanning one band, by rotating the probe for scanning a further band.

In accordance with a further feature of the invention, the probe is formed of a spring steel strip having a perforation and a free end carrying an eddy current scanning head, and the probe drive has a wheel with knobs engaging the perforation.

The probe thus combines the requirement for flexibility for the vertical movement and the requirement for rigidity for the rotary movement in a simple manner.

In accordance with an added feature of the invention, the lifting cylinder has a horizontally extended foot piece, a forked piece and a fastener pivotably linked on the foot piece, a pressure medium controlled or pneumatic cylinder associated with the fastener, a piston rod of the cylinder being connected to the forked piece, the forked piece having a plate-type end, and a clamp holder being attached to the plate-type end for receiving the probe drive.

The pivotability of the probe drive which is thus achieved considerably facilitates the approach of the annular gap.

In accordance with an additional feature of the invention, the clamp holder is attached to the plate-type end at an attachment point having a resiliently supported gap, the clamp holder has a stop and the forked piece has a limit switch holder, together causing an interruption of vertical movement of the probe when a predeterminable gap width is not reached. This is done in order to achieve a run-up protection which is intended to protect the probe from damage.

In accordance with yet another feature of the invention, the spring steel strip has a multiplicity of elongated holes formed therein in a row, defining connecting webs between the elongated holes, the connecting webs have beads with a semicircular cross-section in the opposite direction, and the eddy current scanning head has a transmission line being guided by the beads.

The space-saving accommodation of the transmission lines thus does not result in a weakening of the spring steel strip.

In accordance with a concomitant feature of the invention, the probe is formed of a spring steel strip having a perforation formed therein and having a free end, the probe has a transverse support attached to the free end, the transverse support has a shape corresponding to a curvature of the annular gap and free ends, and the transverse support receives an eddy current scanning head at each of the free ends thereof.

Other features which are considered as characteristic for the invention are set forth in the appended claims.

Although the invention is illustrated and described herein as embodied in a method and a device for non-destructive testing of a penetration of a reactor pressure vessel lid, it is nevertheless not intended to be limited to the details shown, since various modifications and structural changes may be made therein without departing from the spirit of the invention and within the scope and range of equivalents of the claims.

The construction and method of operation of the invention, however, together with additional objects and advantages thereof will be best understood from the following description of specific embodiments when read in connection with the accompanying drawings.

Figure 1:
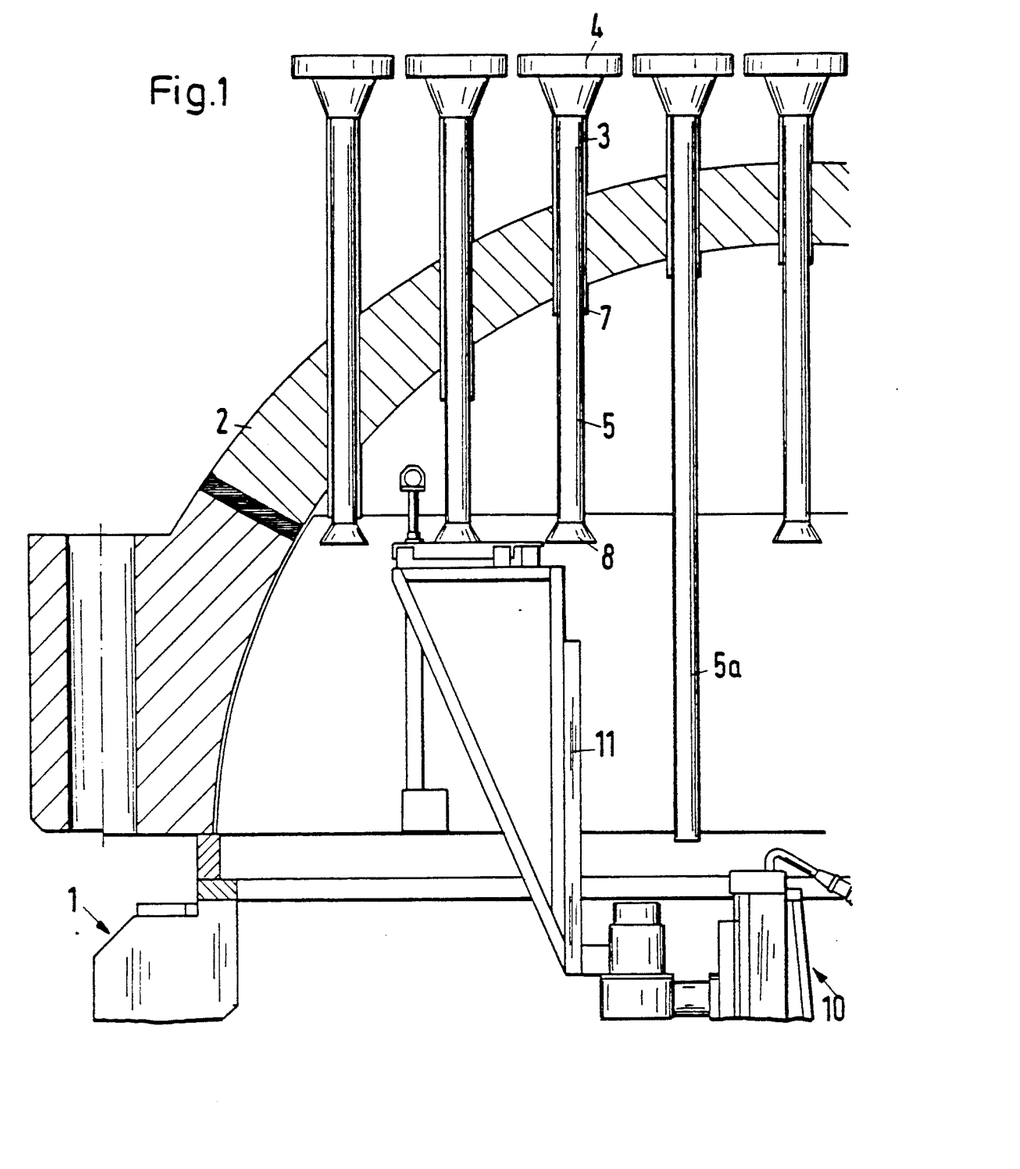
FIG. 1 is a fragmentary, diagrammatic, longitudinal-sectional view of a reactor pressure vessel lid with a diagrammatically indicated test device.
Figure 1A:
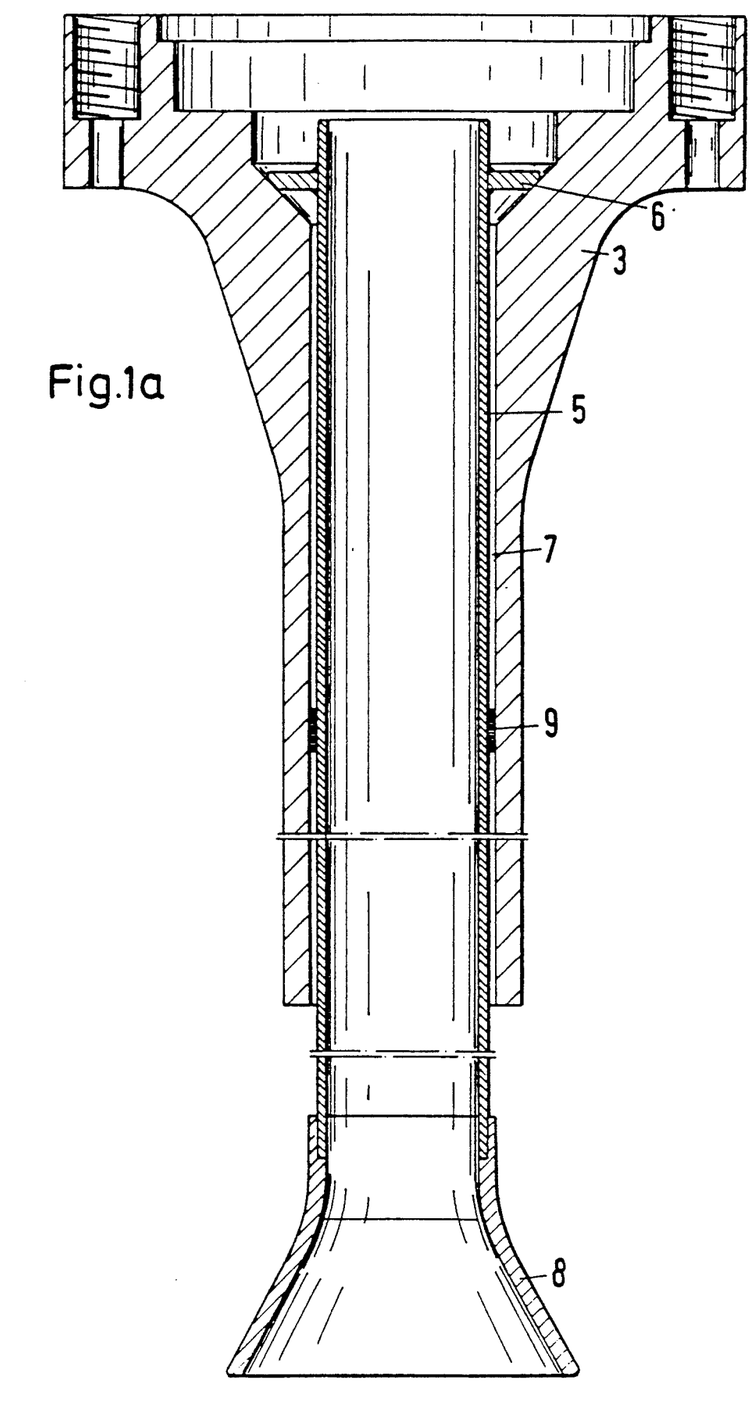
FIG. 1a is an enlarged, longitudinal-sectional view of a connector with a bush supported thereon.

Referring now to the figures of the drawing in detail and first, particularly, to FIG. 1 thereof, there is seen a reactor pressure vessel lid 2 placed on a depositing ring 1. The reactor pressure vessel lid has a plurality of penetrations which are constructed as tubular connectors 3 for non-illustrated control rods. The connectors are welded into the lid 2, they diverge conically at the ends thereof which are situated outside the lid and they merge into a flange 4 for non-illustrated mounting components. Respective connectors 3 are penetrated by a bush 5 or 5a. As can be seen more clearly in FIG. 1a, the bush 5 is supported on the connector 3 by a collar 6 and forms an annular gap 7 which is about 3 mm wide with the connector. Depending on the position of the connector 3, the end of the bush 5 facing the interior of the lid projects further into the interior of the lid 2 than the connector 3 to a greater or lesser extent. The end of the bush 5 projecting from the connector 3 is constructed in the bush 5 as a bell-shaped widening 8. Such a bell-shaped widening can also be omitted, as is shown by the end of the bush 5a projecting further into the interior of the lid 2. The penetration with the bush 5a is otherwise constructed in the same manner as the bush 5 in FIG. 1a. In the region of the connector 3, the bush 5 or 5a is provided with guide knobs 9. A manipulator 10 disposed in the interior of the depositing ring 1 or the lid 2 bears a frame 11, on which a device which is described below and shown in the other figures rests, for testing the connector in the region of the annular gap. The manipulator 10 moves the frame 11 with the parts of the device into a basic position, from which the other components of the device come into the testing position due to their own drive movements.

Figure 2:
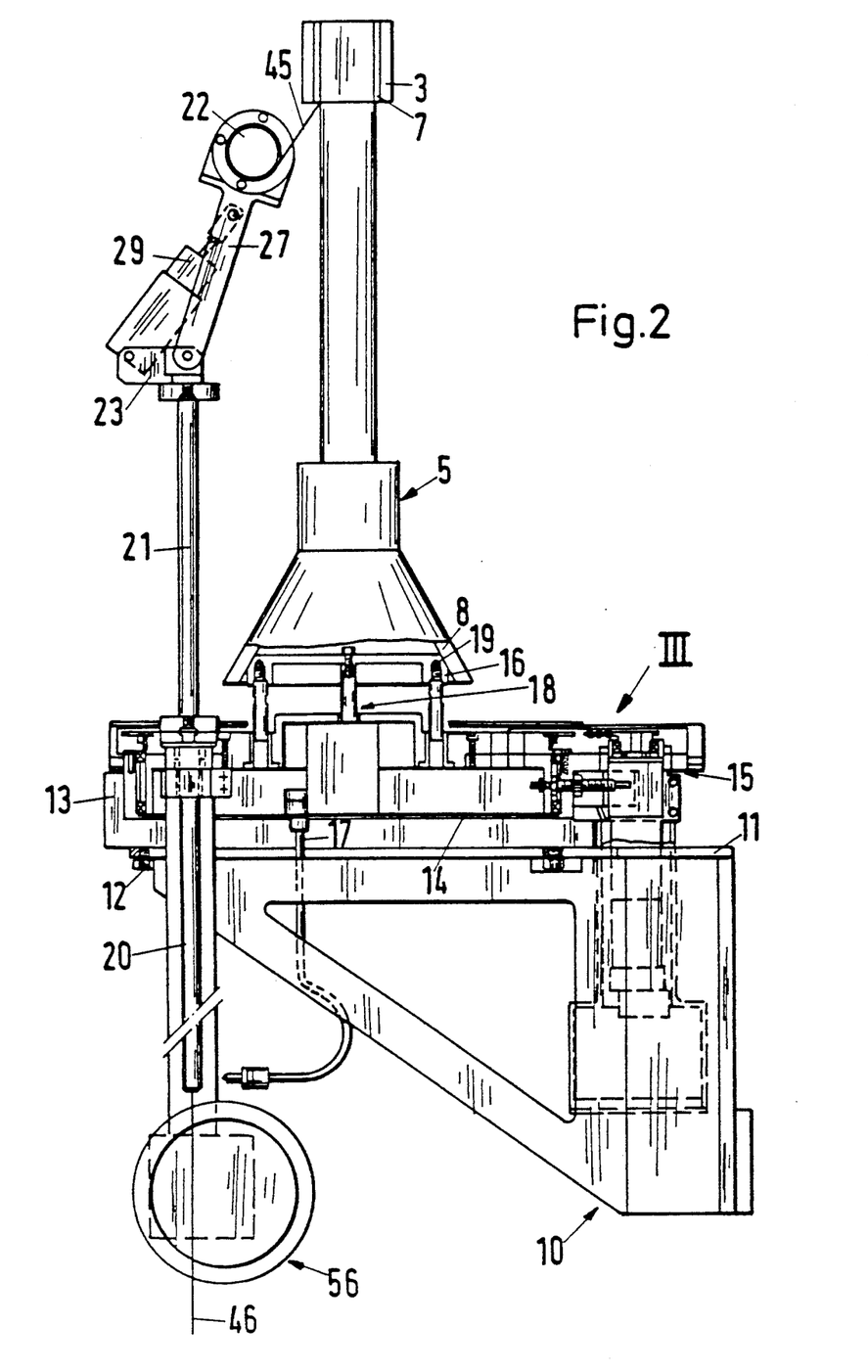
FIG. 2 is a partly broken-away, elevational view of a penetration with the test device.
Figure 3:
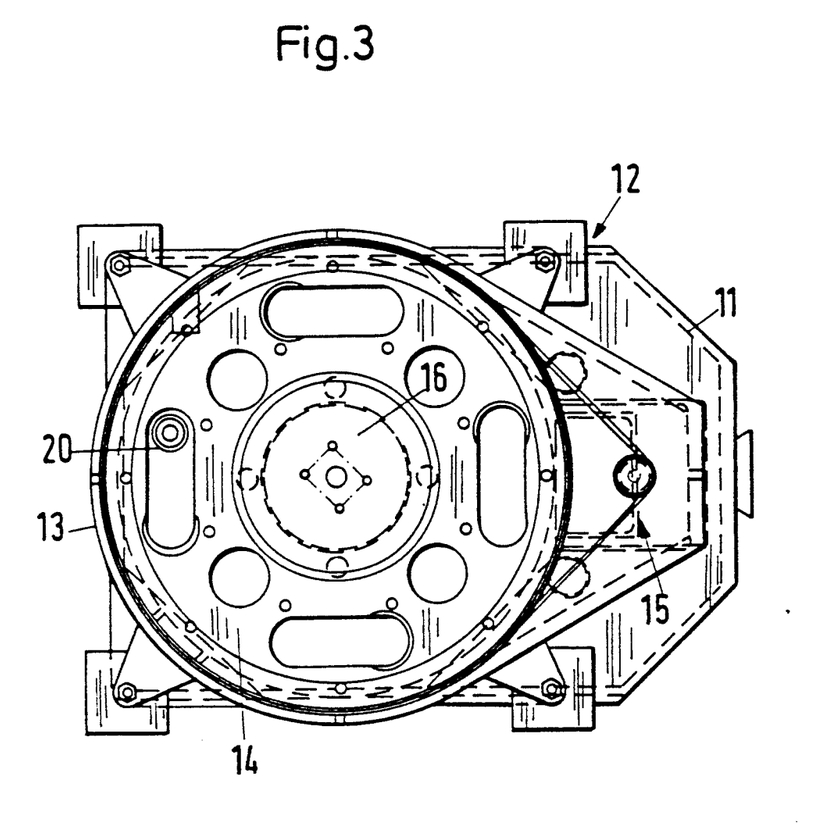
FIG. 3 is a plan view taken in the direction of an arrow III of FIG. 2, with the penetration having been omitted.

FIGS. 2 and 3 show the frame 11 which bears a housing 13 through four floating bearings 12 for receiving a rotary plate 14. The floating bearings allow an oscillating movement up to a deflection of about 5 mm. The rotary plate 14, which is constructed at the periphery thereof as a chain wheel, is set in rotation by a drive unit 15 associated with the housing 13. The center of the rotary plate 14 has a vertically adjustable centering piece 16. In this case, a support 18, which is screwed to the centering piece 16, is vertically movable by a pneumatic connection 17 so that the centering piece 16 contacts the inner peripheral surface of the bell-shaped widening 8 with a predeterminable force. The contact is ensured by an 0-ring 19 associated with the centering piece 16. The pressing force is set in such a way that the bush 5 is raised slightly from a resting surface of the collar 6 and the weight of the bush then rests on the centering piece 16. The support 18 and the centering piece 16 can be removed so that they expose an opening having a clear width which is greater than the diameter of the bush 5a.

In an eccentric configuration shown in FIGS. 2 and 3, the rotary plate 14 is penetrated by an electromechanical lifting cylinder 20, having a piston rod 21 to which a probe drive 22 is linked. The lifting cylinder 20, which is fitted with a drive unit 56, is attached to the rotary plate 14 and, like the centering piece 16, it also carries out the rotary movement of the rotary plate 14. According to FIGS. 5 and 6, a horizontally extended footpiece 23 is screwed to a nut 24 on the piston rod 21 and is secured against rotation by a pin 25. A forked piece 27 is pivotably linked to the footpiece 23 through a bolt connection 26. In the same manner, a fastener 28 for a pneumatic cylinder 29 is connected to the footpiece through a socket pin 26a running parallel to the bolt connection 26. A forked joint 31 which is screwed to the piston rod 30 of the pneumatic cylinder 29 constitutes a connection to a bolt 32 penetrating the upper region of the forked piece 27. The forked joint 31 is held in its position by spacer bushes 33. The three-point connection just described allows a predeterminable pivoting movement of the forked piece 27 by supply lines 34, 35 when the pneumatic cylinder 29 is actuated. A clamp holder 36 is attached to the end of the plate-type structure of the forked piece 27 for receiving an actual probe drive 22 seen in FIGS. 5, leaving a gap 37 which is variable from 0.5 to 3 mm. The gap 37 is made resilient by a plurality of springs 38 which are each embedded in a depression 39. A maximum gap width is adjustable by means of a screw connection 40. In conjunction with liners 42 disposed in the clamp holder 36, at least two stud bolts 41 that are screwed into the end of the plate-type structure of the forked piece 27, guarantee sliding guidance of the clamp holder when the gap width is changed. The spring-mounted construction of the fastener for the probe drive forms a run-up protection for the probe. For this purpose, the clamp holder 36 is associated with an adjustable stop 43 which triggers a limit switch 44 of a limit switch holder 45 attached to the forked piece 27, when a predeterminable gap width is not reached and it interrupts vertical movement of the probe.

Figure 2A:
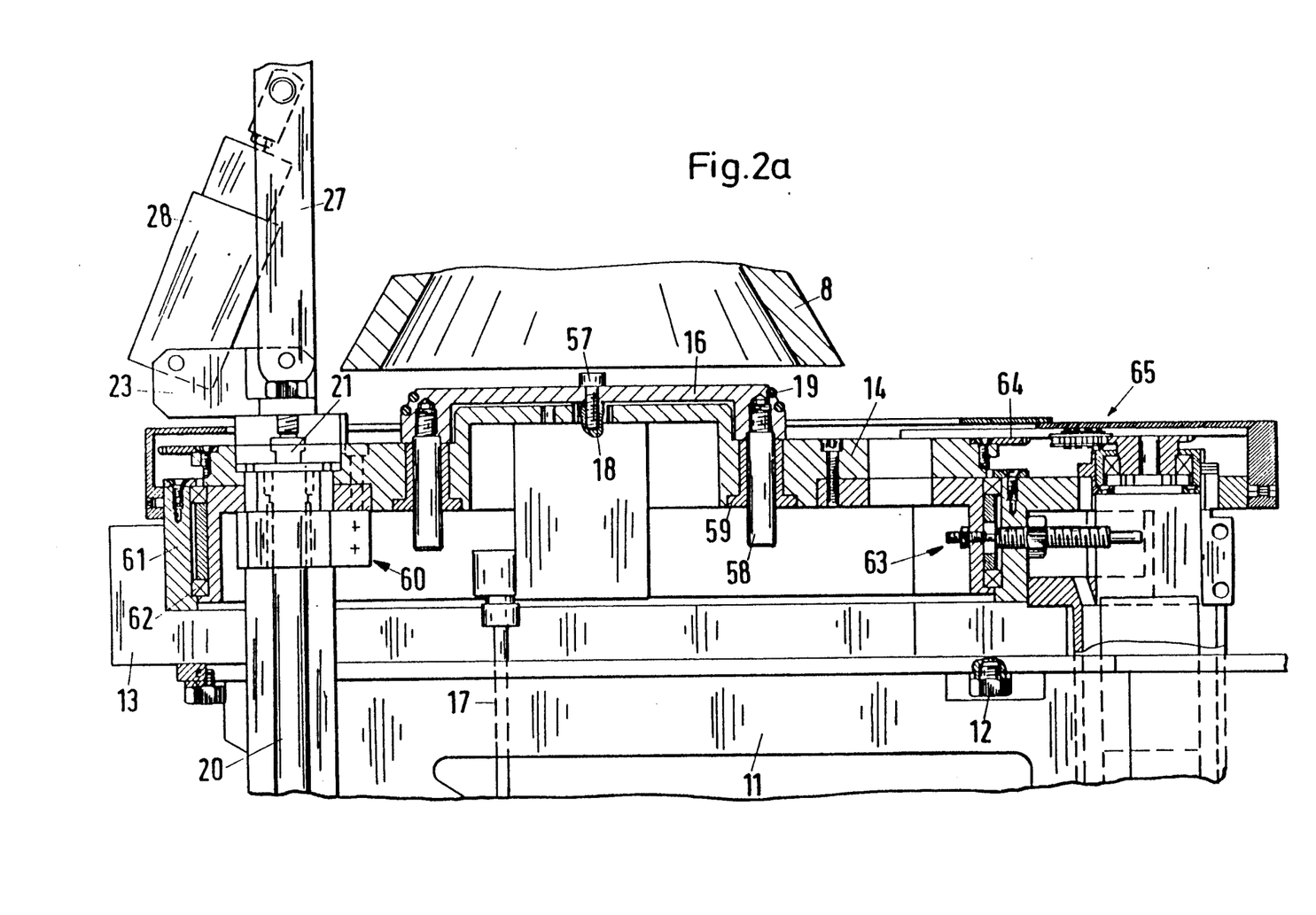
FIG. 2a is an enlarged, fragmentary, elevational view of a portion of FIG. 2.

FIG. 2a shows a portion of FIG. 2 on a larger scale. The centering piece 16, which is attached by a screw 57 to the support 18, has been moved into its lower position, with pins 58 assigned to the centering piece having been guided in liners 59 of the rotary plate 14. The piston rod 21 of the electromechanical lifting cylinder 20, which is attached to the rotary plate 14 with the aid of a tensioning device 60, is also situated in the lower position. The housing 13, which is supported on the frame 11 through the floating bearings 12, is associated with a bearing ring 61, relative to which the rotary plate 14 can carry out an oscillating rotary movement up to 370° with an interposition of a ball bearing 62. The rotary movement can be limited by a limit switch configuration 63. A chained wheel disc 64 is screwed to the rotary plate 14 so that the rotary plate 14 is set in rotation together with the centering piece 16 and the lifting cylinder 20 through the drive unit 15 associated with the housing 13. A chain guard 65 attached to the bearing ring 61 monitors the chain drive.

Figure 7:
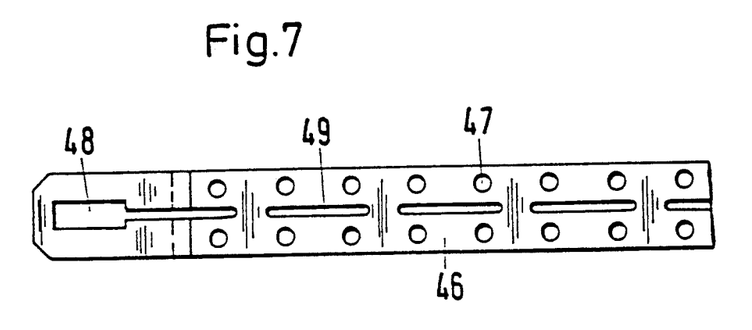
FIG. 7 is a fragmentary, elevational view of a portion of a probe.
Figure 8:
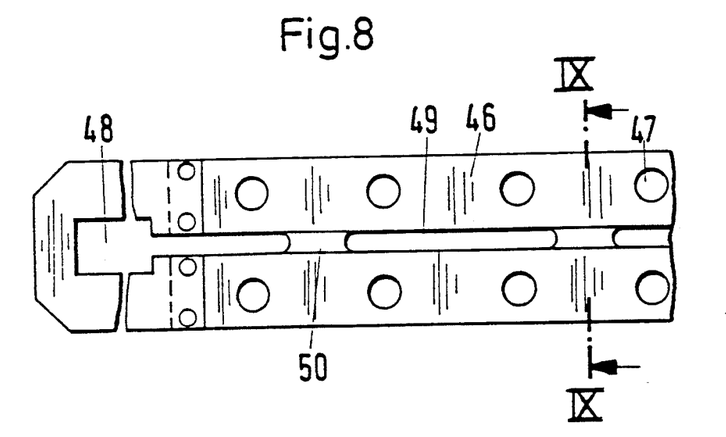
FIG. 8 is an enlarged, fragmentary, elevational view of a portion of a probe.
Figure 9:
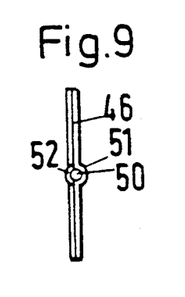
FIG. 9 is a cross-sectional view taken along the line IX—IX of FIG. 8, in the direction of the arrows.

A probe 46 illustrated in FIGS. 7 to 9 is composed of a spring steel strip which has a multiplicity of perforations 47. The probe 46 has an end facing the annular gap 7 to be tested, at which it bears an eddy current scanning head 48.

The spring steel strip is provided with a multiplicity of elongated holes 49 which are disposed in a row, defining remaining connecting webs between the elongated holes being constructed in opposite directions as semicircular beads 51 which serve for guiding a transmission line 50 of the eddy current scanning head 48. The beads 51 contribute to reinforcing the probe without hindering the flexibility required thereof. In order to avoid measuring errors, the portion of the probe bearing the eddy current scanning head 48 is composed of stainless steel with a material number 1.4301 which is applied to the spring steel strip by means of spot-welding 52.

Figure 5:
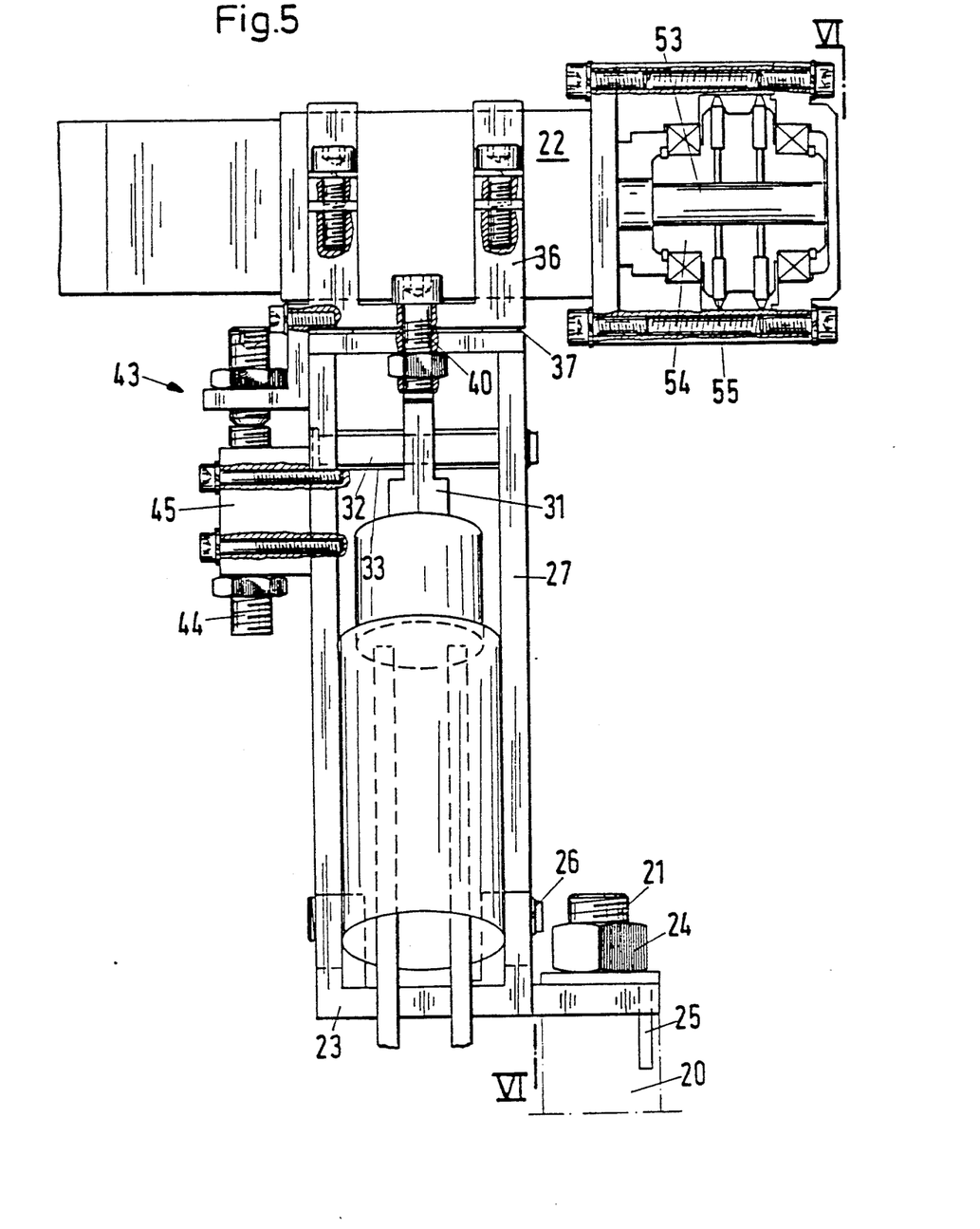
FIG. 5 is an elevational view of a probe drive with connecting elements thereof leading to a lifting cylinder.
Figure 6:
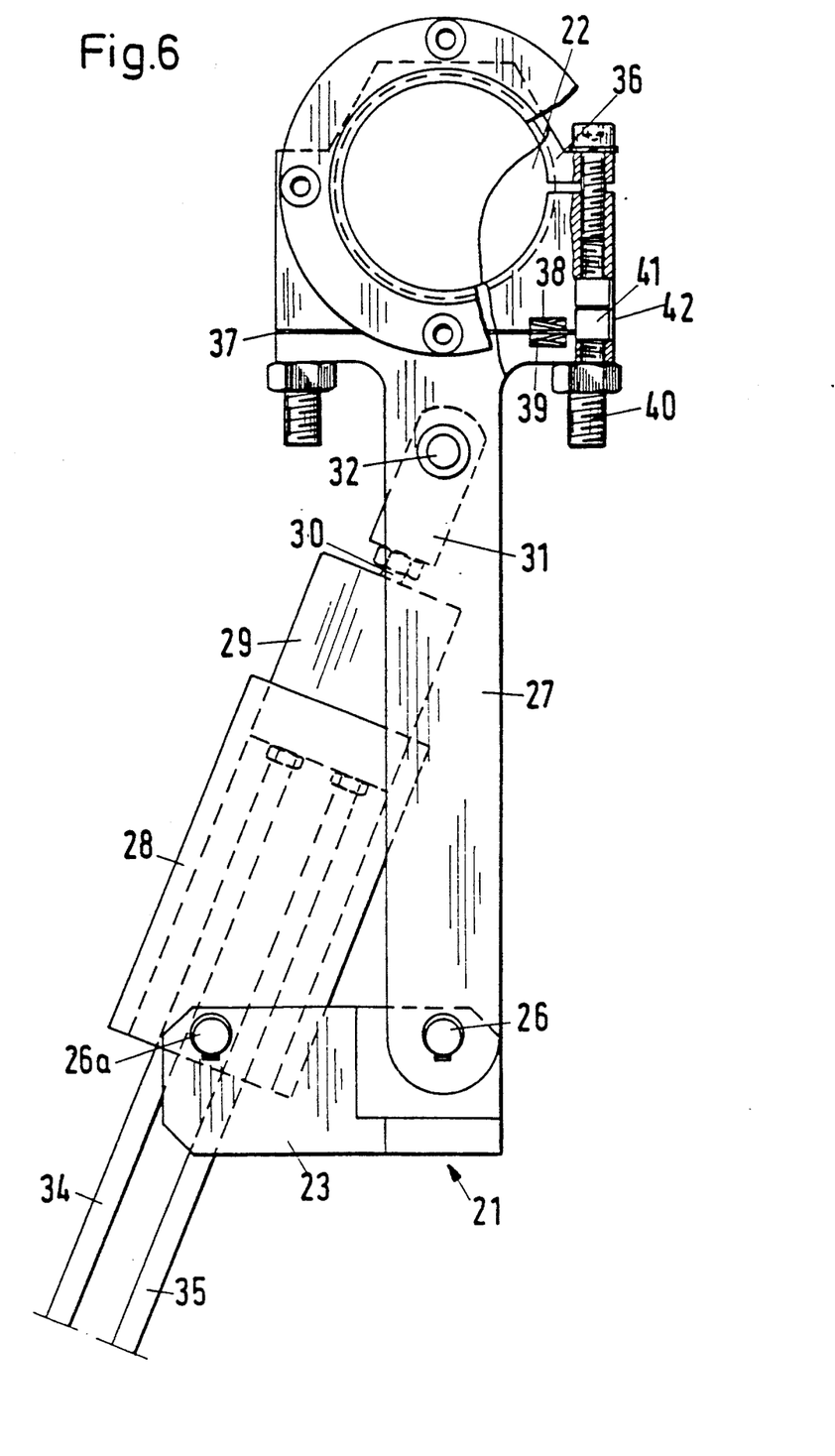
FIG. 6 is a partly broken-away, sectional view taken along the line VI—VI of FIG. 5.

As is seen in FIG. 5, in order to bring about the vertical transport of the probe, a wheel 54 with knobs 55 is associated with an output shaft 53 of the probe drive 22. The knobs 55 are distributed over the periphery of the wheel 54 and they engage in the perforations 47 in the probe 46. The pivotability of the forked piece 27 which is described above with regard to FIGS. 5 and 6 and by means of which the probe likewise carries out a pivoting movement, is indicated above the probe drive in FIG. 2.

Figure 4:
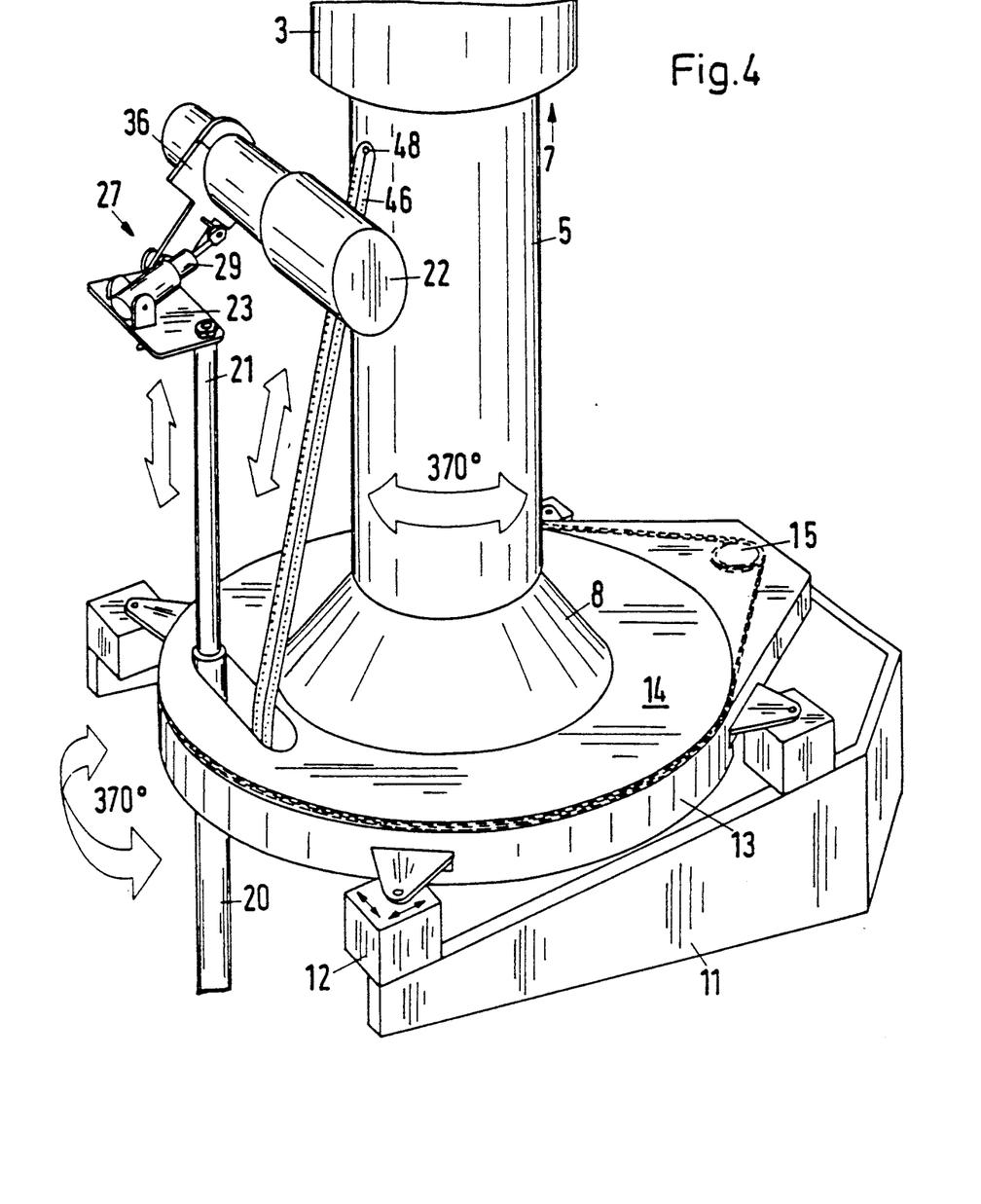
FIG. 4 is a fragmentary, perspective view of the device according to FIGS. 2 and 3.

The execution of the test is explained below with reference to the perspective overview according to FIG. 4. After the test device resting on the frame 11 has been moved with the aid of the manipulator into the vicinity of a reactor pressure vessel lid penetration to be tested, the centering piece 16 will contact the inner peripheral surface of the bell-shaped widening 8 of the bush 5 with a predeterminable force with the aid of the pneumatically displaceable support 18. The probe tip is then positioned in front of the annular gap 7, both by vertical displacement of the probe with the aid of the lifting cylinder and of the probe drive and by pivoting the forked piece 27. A trial rotation of the rotary plate 14 through about 360° provides clarity as to whether or not the centering piece 16 acting as a carrier also rotates the bush during the rotation. If the bush is also rotated, the probe is inserted into the annular gap 7 and moved into a first testing position. The rotary plate is then rotated through about 370°, as a result of which an annular region of the outer surface of the connector 3 is tested, depending on the width of the eddy current scanning head. The probe is then displaced vertically by the probe drive into the next testing position. By rotating the rotary plate through 370° in the opposite direction, an annular region is again tested. This procedure, which carries out vertical displacement plus oscillating movement, is continued until the entire annular gap has been scanned. Since the bush 5 also carries out the rotary movement of the rotary plate, the guide knobs 9, which are disposed on the outer periphery of the bush, do not impede the oscillating movement of the probe. The annular gap 7 to be tested is scanned in a meandering manner by continuous vertical movement during the rotary movement.

However, if it is established during the trial rotation of the centering piece 16 that the bush 5 is not carried along due to contamination or other influences between the bush 5 and the connector 3, the annular space is scanned in a band-type manner by vertical movement of the probe. After one band has been scanned, the next testing position is approached by rotating the rotary plate. In this case, a band occupied by the guide knobs 9 can only be tested below the knobs 9. Upon detection of the guide knobs, the run-up safeguard provides helpful assistance in the region of the spring-mounting between the forked piece 27 and the clamp holder 36.

If the annular gap is to be tested in the region of the bush 5a which has a relatively long construction, as is seen in FIG. 1, the supports 18 and the centering piece 16 are removed. When the device is driven up by the manipulator 10, the bush 5a penetrates the rotary plate 14 so that the device can be moved to the height of the lower ends of the bushes 5. From there, the probe can be inserted into the annular gap in the usual manner. The use of the centering piece 16 is not possible due to the structural length of the bush 5a. If required, guide means engaging the peripheral surface of the bush 5a can take over the task of the centering piece.

Figure 10:
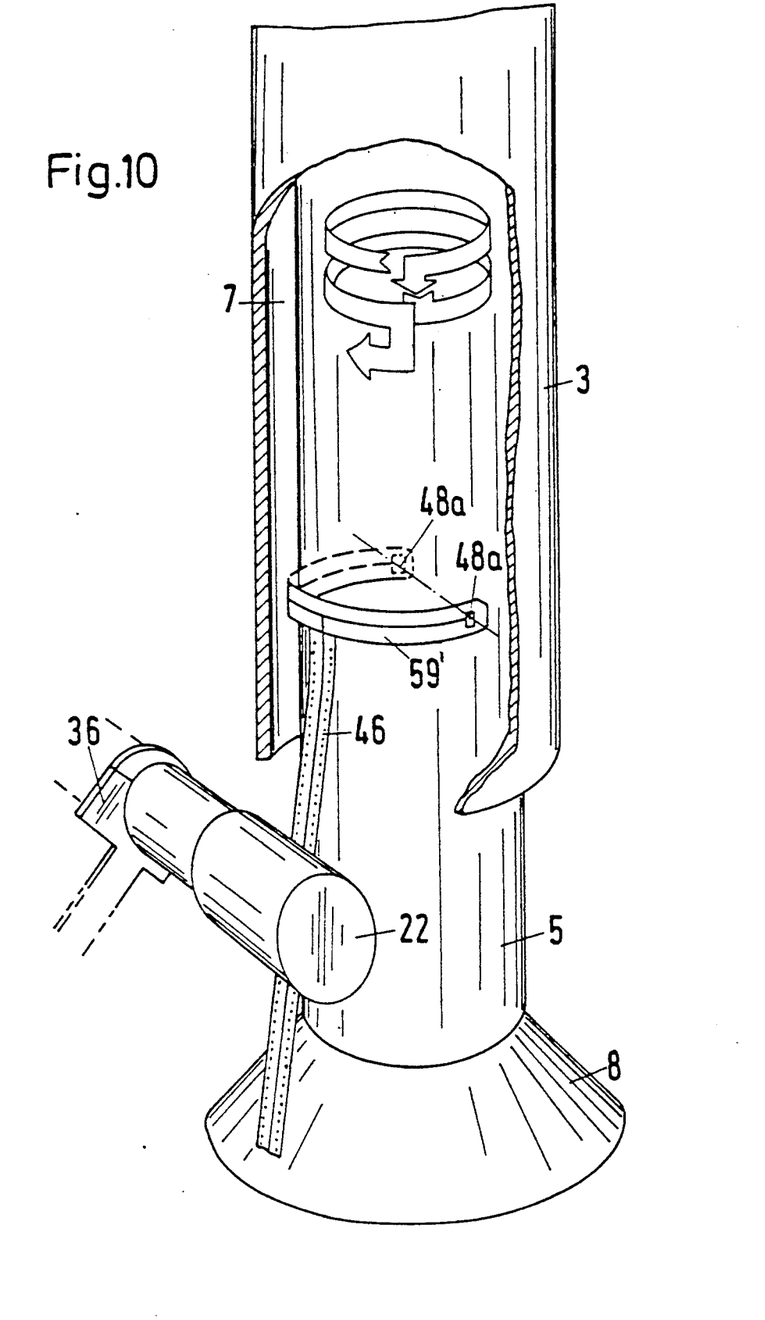
FIG. 10 is a fragmentary, perspective view of another probe structure.

According to FIG. 10, a transverse support 59', corresponding to the curvature of the annular gap 7, is attached to the free end of the probe and bears an eddy current scanning head 48a at each of its free ends. Operation is thus likewise possible with an oscillating method illustrated at the upper end of FIG. 10 with vertical setting of a new testing position. Furthermore, the guide knobs 9 can be avoided more easily when the bush 5 cannot also rotate.

We claim:

1. A method of non-destructively testing a penetration in the form of a connector welded in a reactor pressure vessel lid disposed on a depositing ring, including a bush penetrating and being supported on the connector, defining an annular gap between the bush and the connector, and the bush having a lower end extending further into the interior of the reactor pressure vessel lid than the connector, which comprises defining an annular gap between a connector welded in a reactor pressure vessel lid disposed on a depositing ring and a bush penetrating and being supported on the connector, introducing a probe with an eddy current scanning head into the annular gap defined between the connector and the bush, and displacing the probe in the annular gap.

2. The method according to claim 1, which comprises bringing a centering piece into contact with the lower end of the bush, and setting the probe in rotary movement together with the centering piece and the bush.

3. The method according to claim 2, which comprises oscillating the probe in the rotary movement, and vertically moving the probe into a new testing position at the beginning or end of the oscillating movement.

4. The method according to claim 2, which comprises continuously vertically moving the probe during the rotary movement.

5. The method according to claim 1, which comprises bringing a centering piece into contact with the lower end of the bush, scanning the annular gap with the eddy current scanning head in a band-type manner in a vertical direction while the bush remains in a position of rest, and moving the eddy current scanning head into a new testing position after scanning one band, by rotating the probe for scanning a further band.

6. In a reactor pressure vessel having a depositing ring, a lid being disposed on the depositing ring and having an interior, a penetration in the form of a connector welded in the lid, a bush penetrating and being supported on the connector, defining an annular gap between the connector and the bush, and the bush having a lower end extending further into the interior of the lid than the connector, a device for non-destructively testing the penetration, comprising a manipulator disposed inside the depositing ring, a frame supported on said manipulator, lockable floating bearings on said frame, a housing carried by said bearings, a rotary plate received by said housing, a lifting cylinder having a free end and being eccentrically associated with said rotary plate, said lifting cylinder being vertically adjustable and carrying out a rotary movement of said rotary plate, a probe, and a probe drive disposed at said free end of said lifting cylinder for moving said probe in an axially parallel direction relative to the connector.

7. The device according to claim 6, including a centering piece being concentrically associated with said rotary plate, said centering piece being adjustable in the vertical direction and carrying out the rotary movement of said rotary plate.

8. The device according to claim 6, wherein said probe is formed of a spring steel strip having a perforation and a free end carrying an eddy current scanning head, and said probe drive has a wheel with knobs engaging the perforation.

9. The device according to claim 6, wherein said lifting cylinder has a horizontally extended foot piece, a forked piece and a fastener pivotably linked on said foot piece, a pressure medium controlled cylinder associated with said fastener, a piston rod of said cylinder being connected to said forked piece, said forked piece having a plate-type end, and a clamp holder being attached to said plate-type end for receiving said probe drive.

10. The device according to claim 9, wherein said clamp holder is attached to said plate-type end at an attachment point having a resiliently supported gap, said clamp holder has a stop and said forked piece has a limit switch holder, together causing an interruption of vertical movement of said probe when a predeterminable gap width is not reached.

11. The device according to claim 6, wherein said probe is formed of a spring steel strip having a perforation formed therein and having a free end, said probe has a transverse support attached to said free end, said transverse support has a shape corresponding to a curvature of the annular gap and free ends, and said transverse support receives an eddy current scanning head at each of said free ends thereof.

12. The device according to claim 8, wherein said spring steel strip has a multiplicity of elongated holes formed therein in a row, defining connecting webs between said elongated holes, said connecting webs have beads with a semicircular cross-section in the opposite direction, and said eddy current scanning head has a transmission line being guided by said beads.

13. The device according to claim 11, wherein said spring steel strip has a multiplicity of elongated holes formed therein in a row, defining connecting webs between said elongated holes, said connecting webs have beads with a semicircular cross-section in the opposite direction, and said eddy current scanning head has a transmission line being guided by said beads.

* * * * *